United States Patent [19]

Ramos et al.

[11] Patent Number: 5,183,749
[45] Date of Patent: Feb. 2, 1993

[54] MICROBIAL PROCESS FOR THE PREPARATION OF MILBEMYCIN DERIVATIVES

[75] Inventors: Gerado Ramos, Arlesheim; Oreste Ghisalba, Reinach; Hans-Peter Schär, Aesch; Bruno Frei, Liestal; Peter Maienfisch, Aesch; Anthony C. O'Sullivan, Basel, all of Switzerland

[73] Assignee: Sankyo Company, Ltd., Tokyo, Japan

[21] Appl. No.: 496,183

[22] Filed: Mar. 20, 1990

Related U.S. Application Data

[63] Continuation of Ser. No. 147,956, Jan. 25, 1988, abandoned.

[30] Foreign Application Priority Data

Feb. 4, 1987 [CH] Switzerland .......................... 395/87

[51] Int. Cl.$^5$ ...................... C12P 17/18; C12P 33/06; C12N 1/14; C12N 1/20
[52] U.S. Cl. ........................ 435/119; 435/58; 435/886; 435/917; 435/822; 435/911; 435/254; 435/253.5
[58] Field of Search ................. 435/119, 58, 886, 917, 435/822, 911, 254, 253.5

[56] References Cited

U.S. PATENT DOCUMENTS

| | | | |
|---|---|---|---|
| 3,950,360 | 4/1976 | Aoki et al. | 260/343.2 R |
| 4,173,571 | 11/1979 | Chabala et al. | 260/343.91 |
| 4,226,941 | 10/1980 | Goi et al. | 435/106 |
| 4,328,335 | 5/1982 | Mrozik | 536/7.1 |
| 4,346,171 | 8/1982 | Takiguchi et al. | 435/119 |
| 4,547,520 | 10/1985 | Ide et al. | 514/450 |
| 4,666,937 | 5/1987 | Goegelman | 435/119 |
| 4,696,922 | 9/1987 | Sturm et al. | 514/185 |
| 4,696,945 | 9/1987 | Frei et al. | 514/450 |

FOREIGN PATENT DOCUMENTS

| | | |
|---|---|---|
| 0110667 | 6/1984 | European Pat. Off. |
| 0194125 | 9/1986 | European Pat. Off. |
| 2166436 | 5/1986 | United Kingdom |

OTHER PUBLICATIONS

ATCC Catalogue of Fungi, 1987, pp. 44–46.
Enzymes: Chapter 9: Mechanism, structure, and regulation, ed. Albert L. Lehninger, Worth Publishers, Inc., 1975, pp. 217, 218.

Primary Examiner—Irene Marx
Attorney, Agent, or Firm—Edward McC. Roberts

[57] ABSTRACT

The present invention relates to a one-step microbial process for the preparation of 13β-hydroxy- or 14,15-epoxy-milbemycins of the following formulae I and II

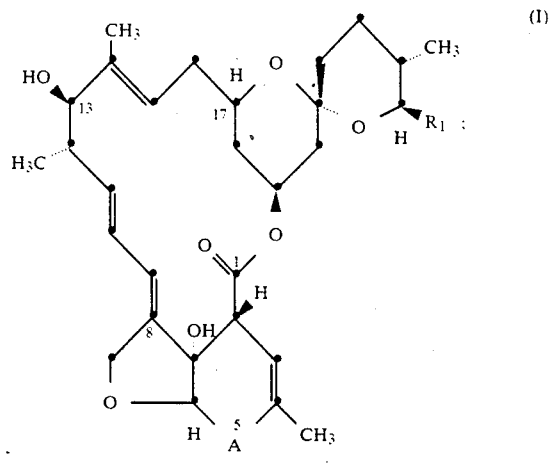

in which
$R_1$ and $R_1'$ represent methyl, ethyl, isopropyl or sec.-butyl or represent the group $$-\underset{\underset{CH_3}{|}}{C}=CH-X$$

in which X represents methyl, ethyl or isopropyl, and A and A' represent the group $$-\underset{\underset{OR_2}{|}}{CH}- \quad \text{or} \quad -\underset{\underset{N\sim OH}{\|}}{C}-$$

in which $R_2$ represents hydrogen, $-C(O)-CH_2O-C(O)-CH_2CH_2-COOH$ or $-C(O)-CH_2CH_2-COOH$, or mixtures of compounds of the formulae I and II, which process comprises bringing a milbemycin of the formula III (Abstract continued on next page.)

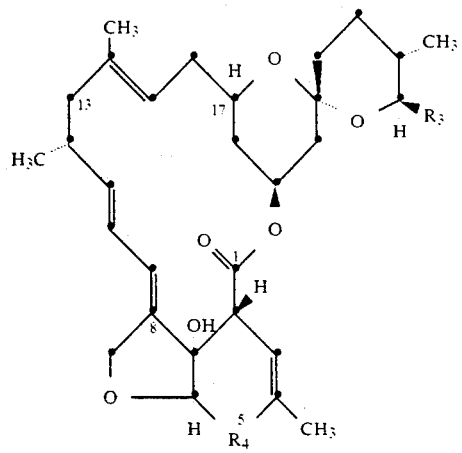
(III)

dissolved in a liquid phase, in which $R_3$ represents $R_1$ or $R_1'$ and $R_4$ represents A or A', and $R_1$, $R_1'$, A and A' have the meanings given for formulae I and II, into contact with a microorganism that is capable of 13β-hydroxylation or 14,15-epoxidation or of both reactions, or into contact with active constituents thereof. The microorganism or its active constituents may be either in free form or immobilized form.

11 Claims, No Drawings

MICROBIAL PROCESS FOR THE PREPARATION OF MILBEMYCIN DERIVATIVES

This application is a continuation of application Ser. No. 07/147,956, filed Jan. 25, 1988, now abandoned.

The present invention relates to a one-step microbial process for the preparation of 13β-hydroxy- and 14,15-epoxy-milbemycins of the following formulae I and II

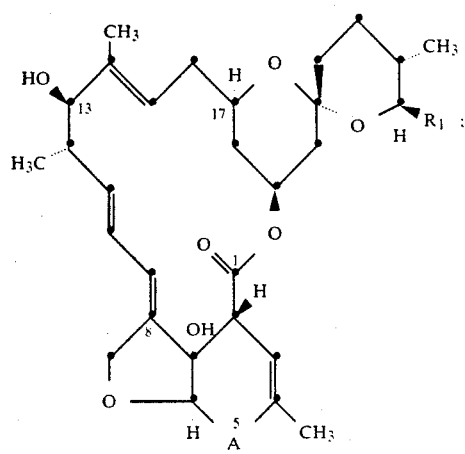

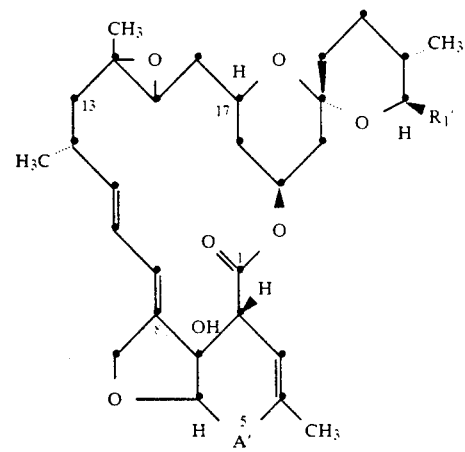

in which
$R_1$ and $R_1'$ represent methyl, ethyl, isopropyl or sec.-butyl or represent the group

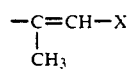

in which X represents methyl, ethyl or isopropyl, and
A and A' represent the group

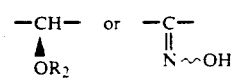

in which $R_2$ represents hydrogen, —C(O)—CH$_2$O—C(O)—CH$_2$CH$_2$—COOH or —C(O)—CH$_2$CH$_2$—COOH, or mixtures of compounds of the formulae I and II, which process comprises bringing a milbemycin of the formula III

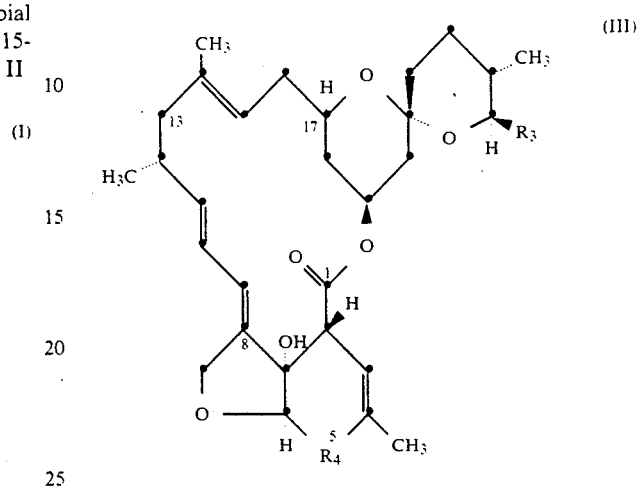

dissolved in a liquid phase, in which $R_3$ represents $R_1$ or $R_1'$ and $R_4$ represents A or A', and $R_1$, $R_1'$, A and A' have the meanings given for formulae I and II, into contact with a biocatalyst that is capable of 13β-hydroxylation or 14,15-epoxidation or of both reactions, for a period of time that is sufficient for carrying out the 13β-hydroxylation or 14,15-epoxidation reaction or both reactions.

Especially preferred within the scope of this invention is a process for the preparation of compounds of the following formulae I and II

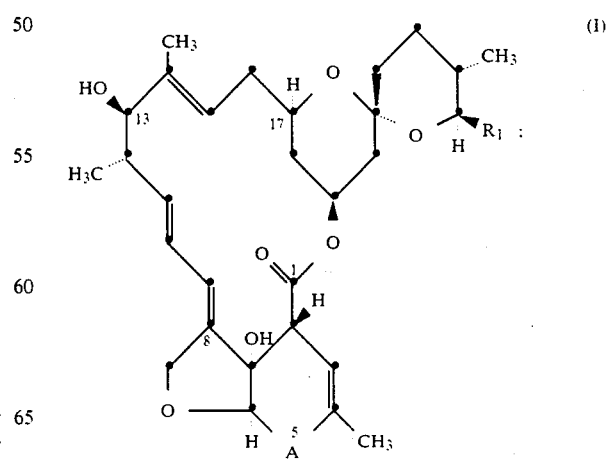

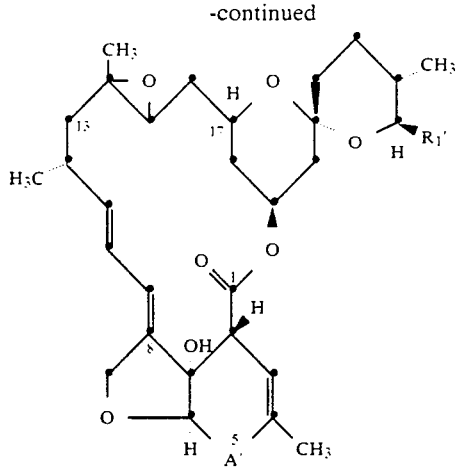

in which
R₁ and R₁' represent methyl, ethyl, isopropyl or sec.-butyl and
A and A' represent the group

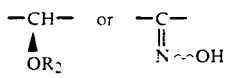

in which R₂ represents hydrogen, —C(O)—CH₂O—C(O)—CH₂CH₂—COOH or —C(O)—CH₂CH₂—COOH.
which comprises bringing a milbemycin of the formula III

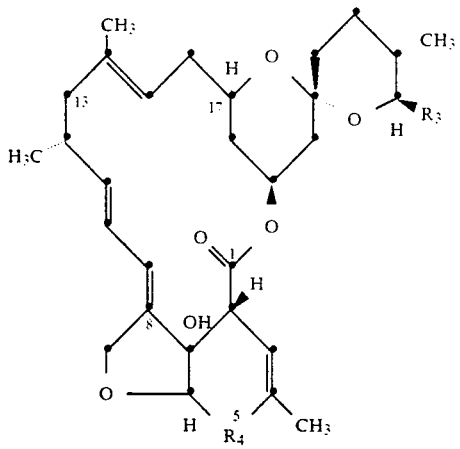

dissolved in a liquid phase, in which
R₃ represents methyl, ethyl, isopropyl or sec.-butyl and
R₄ represents the group

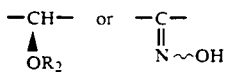

in which R₂ represents hydrogen, —C(O)—CH₂O—C(O)—CH₂CH₂—COOH or —C(O)—CH₂CH₂—COOH
into contact with a biocatalyst that is capable of 13β-hydroxylation or 14,15-epoxidation or of both reactions for a period of time that is sufficient for carrying out the 13β-hydroxylation or 14,15-epoxidation reaction or both reactions.

Compounds of the formulae I and II in which R₁ and R₁' represent the group

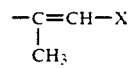

and the radicals X, A, A' and R₂ have the meanings given for formulae I and II represent such 23-deoxy derivatives of natural antibiotics S541 that contain a 13β-hydroxy group or a 14,15-epoxy group and that carry either a free OH group or an oxime grouping at the 5-position.

In this microbial process, in general both products (I) and (II) are formed, but (I) is ordinarily formed in excess, the products (I) and (II) usually being obtained in a ratio of approximately 4:1.

The two reaction products of the formulae I and II obtained in this manner may be separated from one another without great technical expenditure by means of customary separating methods, for example by fractional crystallisation or by chromatography. Chromatography includes, for example, column chromatography, thick layer chromatography or thin layer chromatography on mineral carrier materials such as silica gel or on organic exchanger resins.

If only compounds of the formula I (13β-hydroxymilbemycins) are of interest, then the separation of (I) and (II) is not necessary, since the 14,15-epoxides of the formula II can be converted into 13β-hydroxymilbemycins of the formula I in accordance with EP-0,180,539.

Within the scope of the present invention, the terms "microorganism" and "active constituents thereof" are to include:
a) the living microorganism in the form of vegetative cells,
b) the dead microorganism, preferably in a disintegrated form, that is to say with cell wall/cell membrane mechanically or chemically disrupted or removed,
c) crude extracts of the cell contents of the said microorganism,
d) the enzymes that convert the compounds of the formula III into compounds of the formula II and/or I, and
e) the spores of the said microorganism.

The active systems mentioned under a) to e) that can be used in accordance with the invention shall here and hereinafter, for the sake of simplicity, be summarised by the term biocatalysts, and this term shall be used to represent any of these systems.

Bacteria and higher fungi are especially suitable microorganisms for the process according to the invention. Suitable bacteria are especially representatives of Actinomycetes, especially of the genus Streptomyces; the strains Streptomyces diastatochromogenes ATCC 31561, and especially Streptomyces violascens ATCC 31560, have proved particularly suitable for the stereospecific introduction of a hydroxy group into the 13β-position and/or for a 14,15-epoxidation of compounds of the formula III. Especially suitable among the higher fungi are representatives of Fungi imperfecti, especially representatives of the Moniliales group. It is possible to obtain especially good results as regards the products of the formulae I and II by using representatives of the genus Aspergillus, especially the strain *Aspergillus niger* sp. KS-101 ATCC 20567.

The microorganisms used within the scope of this invention, i.e. the Streptomyces strains *Streptomyces diastatochromogenes* ATCC 31561 and *Streptomyces violascens* ATCC 31560 and also the Aspergillus strain *Aspergillus niger* sp. KS-101 ATCC 20567, are described in U.S. Pat. No. 4,226,941.

That description, which covers columns 3 to 6 of the said U.S. Patent, forms part of the present invention in the form of a reference.

The 13β-hydroxymilbemycins of the formula I having a free or acylated 5-hydroxy group are disclosed in EP-0,180,539 as exceedingly active antiparasitic agents for controlling ecto- and endoparasites on and in productive livestock. In the known process (EP-0,180,539) for the preparation of compounds of the formula I, as in the microbial process according to the invention, compounds of the formula III are used as starting materials. In the known process, in a first step compounds of the formula III are converted with peracids into the 14,15-epoxides of the formula II:

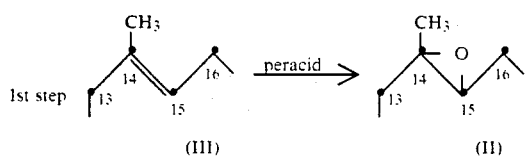

and the 14,15-epoxides of the formula II are then reacted with the aid of a special complex reagent to form 15-hydroxy compounds of the formula IV:

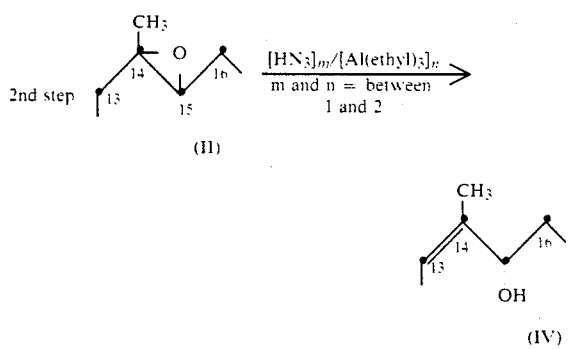

In a further step, the 15-hydroxy compounds of the formula IV are then reacted with chromate, halochromate or dichromate ions, especially pyridinium dichromate:

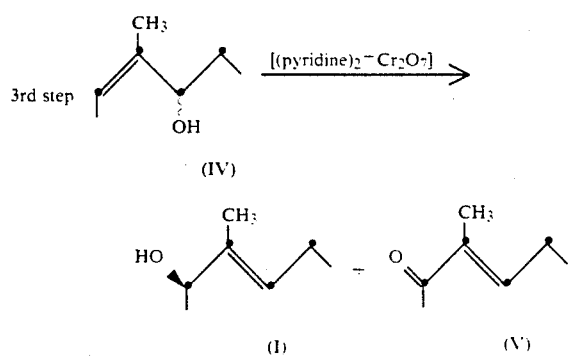

there also being formed, in addition to the desired 13-hydroxymilbemycins of the formula I, 13-oxo compounds which have to be removed.

Compared with the known process, the microbial hydroxylation process according to the invention has the decided advantage that it comprises only one step, results in higher total yields and is ecologically safer since fewer chemicals have to be used, and biomass only is formed as a secondary product.

The 14,15-epoxide resulting from the microbial process according to the invention is known, for example from the following European A-specifications: EP-0,180,539, EP-0,147,852, EP-0,184,989 and EP-0,184,173, as a valuable building block for the preparation of variously substituted milbemycins.

The compounds of the formulae I and II in which A and A' represent an oxime group are novel and are themselves highly active ecto- and endo-parasiticides or intermediates for the preparation of highly active ecto- and endo-parasiticides.

The following subgroups of compounds of the formulae I and II are especially preferred owing to their pronounced parasiticidal and insecticidal activity:

Group Ia, IIa: Compounds of the formulae I and II in which $R_1$ and $R_1'$ represent methyl, ethyl, isopropyl or sec.-butyl, or the group

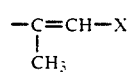

in which X represents methyl, ethyl or isopropyl, and A and A' represent the group

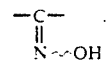

Group Ib, IIb: Compounds of the formulae I and II in which $R_1$ and $R_1'$ represent methyl, ethyl, isopropyl or sec.-butyl and A and A' represent the group

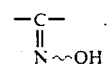

Group Ic, IIc: Compounds of the formulae I and II in which $R_1$ and $R_1'$ represent methyl or ethyl and A and A' represent the group

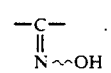

Most especially preferred are the individual compounds listed below:
14,15-epoxy-5-oximino-milbemycin $A_4$
14,15-epoxy-5-oximino-milbemycin $A_3$
14,15-epoxy-5-oximino-milbemycin D.

Milbemycins are known from the literature as highly active ecto-and endo-parasiticides, for example those of the following formula (M):

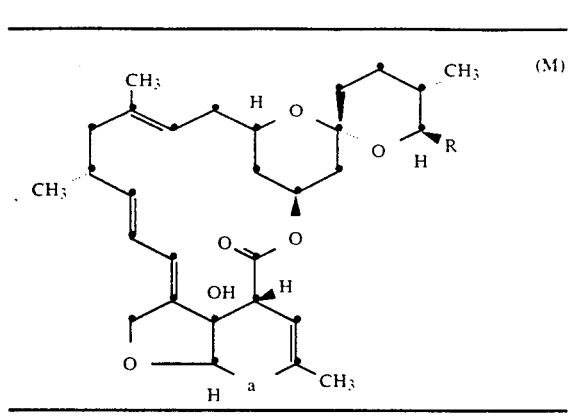

| | | |
|---|---|---|
| R = CH₃, a = —CH—<br>                  │<br>                  OH | = | milbemycin A₃ from<br>U.S. Pat. No. 3,950,360 |
| R = C₂H₅, a = —CH—<br>                  │<br>                  OH | = | milbemycin A₄ from<br>U.S. Pat. No. 3,950,360 |
| R = isoC₃H₇, a = —CH—<br>                     │<br>                     OH | = | milbemycin D from<br>U.S. Pat. No. 4,346,171 |
| R = sec.C₄H₉, a = —CH—<br>                       │<br>                       OH | = | 13-deoxy-22,23-dihydro-C-076-<br>B1a-aglycon,<br>from U.S. Pat. No. 4,173,571. |
| R = CH₃, a = —C—<br>                ‖<br>                N—OH | = | 5-oxime-milbemycin A₃ from<br>U.S. Pat. No. 4,547,520 |
| R = C₂H₅, a = —C—<br>                 ‖<br>                 N—OH | = | 5-oxime-milbemycin A₄ from<br>U.S. Pat. No. 4,547,520 |
| R = isoC₃H₇, a = —C—<br>                    ‖<br>                    N—OH | = | 5-oxime-milbemycin D from<br>U.S. Pat. No. 4,547,520 |

Compounds in which R represents sec.-butyl shall here and hereinafter also be considered as milbemycin derivatives although according to conventional classification they are derived from avermectin derivatives. Avermectin-aglycones (with an OH group in the 13-position) can, however, be converted into milbemycin homologues in accordance with U.S. Pat. No. 4,173,571.

The constitution of natural antibiotics S541 is known from DE-OS 35 32 794 and is as follows:

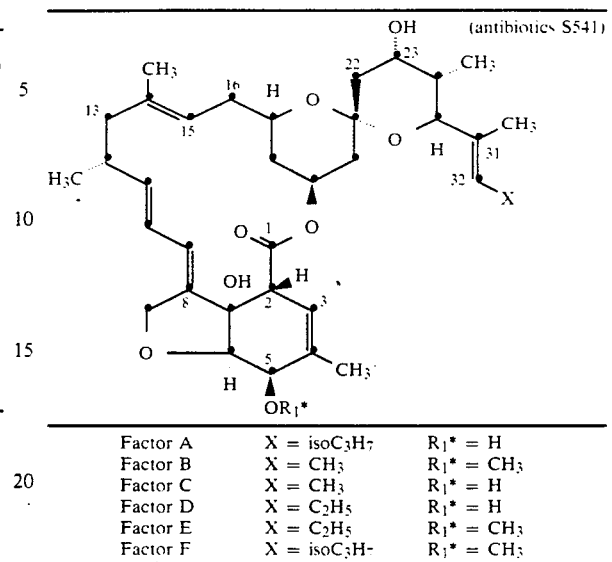

| | | |
|---|---|---|
| Factor A | X = isoC₃H₇ | R₁* = H |
| Factor B | X = CH₃ | R₁* = CH₃ |
| Factor C | X = CH₃ | R₁* = H |
| Factor D | X = C₂H₅ | R₁* = H |
| Factor E | X = C₂H₅ | R₁* = CH₃ |
| Factor F | X = isoC₃H₇ | R₁* = CH₃ |

In the following, in order to simplify the nomenclature the derivatives of antibiotic S541 are classified corresponding to these factors as derivatives of S541A, S541B, S541C, S541D, S541E or S541F.

Compounds of the formula III in which $R_3$ represents the group

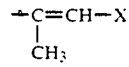

wherein the radicals X and $R_4$ have the meanings given for formula III and which can be used as starting materials in the process according to the invention, can be produced in a manner known per se from the natural antibiotics S541.

The hydroxy group in the 23-position in the antibiotics S541 can be removed analogously to the method disclosed in U.S. Pat. No. 4,328,335, and the antibiotics S541 can thus be converted into the corresponding 23-deoxy derivatives. Those compounds having a free 5-OH group ($R_1^*$ =H) must first be protected selectively be reaction with one of the silylation reagents Y—Si($R_5$)($R_6$)($R_7$) indicated hereinafter or with tert.-butyldimethylsilyloxyacetyl chloride. The reaction of those protected compounds in which $R_1^*$ has been replaced by Si($R_5$)($R_6$)($R_7$) or C(=O)CH₂OSi(CH₃)₂t—C₄H₉ and the 23-C atom has been substituted by OH, with p-methylphenyl-chlorothionoformate yields derivatives of the antibiotics S541 that are substituted at the 23 position by —O—C(=S)—OC₆H₄—CH₃—p. These 23-O-(4-methylphenoxy)-thiocarbonyl derivatives of antibiotics S541 are then used as starting materials for reduction with tributyltin hydride in toluene in the presence of azobisisobutyronitrile at from 80° C. to 120° C. to form the corresponding 23-deoxy derivatives (position 23 substituted).

For the silylation it is expedient to use a silane of the formula Y—Si($R_5$)($R_6$)($R_7$), wherein each of $R_5$, $R_6$ and $R_7$, preferably independently of the others, represents $C_1$–$C_4$-alkyl, benzyl or phenyl and the radical —Si($R_5$)($R_6$)($R_7$) forms, for example, one of the following groups: trimethylsilyl, tris(tert.-butyl)silyl, dimethyl(2,3-dimethyl-2-butyl)-silyl, diphenyl-tert.-butylsilyl, bis(isopropyl)methylsilyl, triphenylsilyl etc. and especially tert.-butyldimethylsilyl. Y is a silyl-leaving group such as, for example, a bromide, chloride, cyanide, azide, acetamide, trifluoroacetate or trifluoromethanesulphonate. This list does not constitute a limitation; further typical silyl-leaving groups are known to the skilled person.

5-O-silylations are carried out in an anhydrous medium, preferably in inert solvents and, most preferably, in aprotic solvents. The reaction advantageously takes place in a temperature range of +80° C., preferably from +10° C. to +40° C. It is preferred to add an organic base. Examples of suitable organic bases are tertiary amines such as triethylamine, triethylenediamine, triazole and, preferably, pyridine, imidazole or 1,8-diazabicyclo[5.4.0]undec-7-ene (DBU).

The removal of these silyl radicals at the 5-position is effected in a manner known per se by selective mild hydrolysis with, for example, an arylsulphonic acid in an alcoholic solution or in accordance with another method familiar to the skilled person.

The preparation of the oximes [$R_4$=—C(=N—OH)—] within the scope of formula III is effected by reacting a derivative of the formula III, in which $R_4$ has been replaced by —C(O)—, with hydroxylamine or a salt thereof, preferably with a mineral acid salt thereof, especially a hydrochloride. The reaction is advantageously carried out in a suitable solvent, for example a lower alkanol, such as methanol, ethanol, propanol; an ethereal compound, such as tetrahydrofuran or dioxan; an aliphatic carboxylic acid, such as acetic acid or propionic acid; water; or in mixtures of these solvents with one another or with other customary inert solvents. The reaction temperatures may vary within wide ranges. The reaction is advantageously carried out, for example, within a range of from +10° C. to +100° C. If hydroxylamine is used in the form of one of its salts, for example in the form of a hydrochloride, it is advantageous if, to intercept the acid (for example HCl), one of the bases customary for such purposes is added, and the operation is optionally carried out in the presence of a water binder, for example a molecular sieve. Suitable bases are organic and inorganic bases, for example tertiary amines such as trialkylamines (trimethylamine, triethylamine, tripropylamine etc.), pyridine and pyridine bases (4-dimethylaminopyridine, 4-pyrrolidylaminopyridine etc.), oxides, hydrides and hydroxides, carbonates and hydrogen carbonates of alkali metals and alkaline earth metals (CaO, BaO, NaOH, KOH, NaH, Ca(OH)$_2$, KHCO$_3$, CH$_3$COONa or CH$_3$COOK. Furthermore, alkali alcoholates such as C$_2$H$_5$ONa, n-C$_3$H$_7$ONa etc. are also suitable. Triethylamine is preferred.

The derivatives of formula III in which $R_4$ represents —C(O)— can be prepared from the corresponding natural antibiotics S541 (S541A, S541C, S541D) and from the milbemycins of the formula M, by mild oxidation with, for example, brownstone (MnO$_2$), CrO$_3$/pyridine or by Oppenauer oxidation.

Compounds of the formula III in which $R_4$ represents —C(O)—CH$_2$O—C(O)—CH$_2$CH$_2$COOH or —C(O)—CH$_2$CH$_2$—COOH can be preparred from the corresponding milbemycins and from the natural antibiotics S541 analogously to known methods by esterification.

The process according to the invention is, in detail, carried out as follows:

To prepare compounds of the formula I or compounds of the formula II or mixtures of the two, a compound of the formula III and a biocatalyst that is suitable for the stereospecific introduction of a hydroxy group into the 13β-position and/or for a 14,15-epoxidation of the compounds of the formula III, or for both reactions, are brought into direct contact with each other, and this contact is maintained for a period of time that is sufficient for the hydroxylation and/or epoxidation.

Most expediently, the process is carried out by culturing a microorganism that is capable of carrying out the hydroxylation/epoxidation reaction according to the invention, under controlled conditions in the presence of a compound of the formula III, and maintaining the joint incubation of the said microorganism and its substrate until a majority of the added compound of the formula III, preferably from 80 to 99.9%, has been converted into compounds of the formula I or II or a mixture of these compounds.

The isolation of the resulting compounds of the formula I or II, or of the mixture containing the two compounds, can be carried out in a manner known per se, for example with the aid of silica gel chromatography.

Compounds of the formula III are used as a substrate for the hydroxylation reaction according to the invention. These compounds are known (see, for example, formula M) or can be prepared from known compounds analogously to known processes. They are suitable for controlling pests on and in animals and plants and are furthermore valuable starting materials or intermediates in the preparation of compounds of the formula I.

The preparation of compounds of the formula I can also be carried out by using for the hydroxylation of the compounds of the formula III not the microorganism itself but active constituents originating from this microorganism (according to the definitions b to d above) that are suitable for the hydroxylation. It is also possible in this manner to prepare the epoxy compounds of the formula II and mixtures of the two compounds.

When using microbial spores instead of vegetative cell structures, the said spores are harvested from microorganisms that are suitable for the stereospecific 13β-hydroxylation or 14,15-epoxidation of compounds of the formula III, or for both reactions, and are then incubated with a compound of the formula III for a period of time that is sufficient for the corresponding reaction(s) to take place. The incubation of spores and substrate is preferably carried out in the absence of culture medium in order to prevent the spores from germinating.

A further aspect of the present invention is the use in immobilised form of vegetative microorganism cells, cell-free extracts, spores, enzymes and mixtures of enzymes of the said microorganisms that are suitable for a stereospecific introduction of a 13β-hydroxy group or for the 14,15-epoxidation of compounds of the formula III, or for both reactions.

The immobilisation of the said biocatalysts can be carried out analogously to processes known per se.

Within the scope of the present invention there may be mentioned especially processes that are based on adsorptive binding or ionic or covalent bonding of the said biocatalysts to solid, as a rule water-insoluble, carrier materials, on crosslinking of biocatalysts by bi- or poly-functional reagents, on matrix encapsulation, on membrane separation or on a combination of two or more of the abovementioned processes.

The adsorptive binding to water-insoluble carriers (adsorbants) is carried out especially by van der Waals forces. Numerous inorganic and organic compounds and also synthetic polymers are suitable as adsorbants.

Methods for such an immobilisation of microorganisms are described by van Haecht et al., 1985 (yeast cells/glass), Black et al., 1984 (yeast cells/refined steel, polyester), Wiegel and Dykstra, 1984 (clostridia/cellulose, hemicellulose), Förberg and Häggström, 1984 (clostridia/wood shavings) and also by Ehrhardt and Rehm, 1985 (Pseudomonads/active carbon). Corresponding details for the use of enzymes immobilised by adsorptive binding are to be found in Krakowiak et al., 1984 (glucoamylase/aluminium oxide), Cabral et al., 1984 (glucoamylase/titanium-activated glass), Miyawaki and Wingard 1984 (glucose oxidase/active carbon), Kato and Horikoshi, 1984 (glucose transferase/synthetic resin) inter alia.

Ionic bonds are based on electrostatic attractions between oppositely charged groups of the carrier material (such as, for example, commercially available ion exchangers, for example based on polysaccharides or on synthetic resins) and of the biocatalyst to be bound.

Methods of immobilising microorganisms based on ionic bonding are described by DiLuccio and Kirwan, 1984 (Azotobacter spec./Cellex E (cellulose)) and by Giard et al., 1977 (animal cells/DEAE-Sephadex).

A corresponding immobilisation of enzymes can be carried out in accordance with the details given by Angelino et al., 1985 (aldehyde oxidase/octylamino-Sepharose 4B), Hofstee, 1973 (lactate dehydrogenase/octylamino-Sephadex), Kühn et al., 1980 (glucose oxidase/DEAE-Sephadex, DEAE-cellulose) and others.

A further method of immobilisation is based on the use of covalent bonding forces, which generally result in fixed linking of biocatalysts to one another or between biocatalyst and carrier material, it being possible to use as carrier materials porous materials, such as glasses, silica or other insoluble inorganic materials.

Within the scope of the process according to the invention, the microorganisms can be immobilised, for example, analogously to Messing and Oppermann, 1979 (Enterobacteria/borosilicate glass; yeast cells/zirconium oxide), Romanovskaya et al., 1981 (methane bacteria/Silochrome), Navarro and Durand, 1977 (yeast cells/porous silica).

The immobilisation of enzymes can be carried out in accordance with the method described by Weetall and Mason, 1973 (papain/porous glass) and Monsan et al., 1984 (invertase/porous silica).

In the process according to the invention not only are the carrier materials already mentioned suitable for immobilisation but also a whole series of natural or synthetic polymers, such as, for example, cellulose, dextran, starch, agarose etc. or polymers, for example based on acrylic and methacrylic acid derivatives, that are usually used in the manufacture of reactive copolymers. Suitable reactive groups by means of which a bond to the biocatalyst is formed are reactive dinitrofluorophenyl or isothiocyanate groups, especially oxirane and acid anhydride groups. A further possibility resides in the chloride activation of resins carrying carboxy groups, which are commercially available, for example, under the trade names Amberlite ® XE-64 and Amberlite ® IRC-50.

The immobilisation of microorganisms with the aid of natural or synthetic carrier materials can be carried out as described by Chipley, 1974 (Bacillus subtilis/agarose), Gainer et al., 1980 (Azotobacter species/cellulose), Jack and Zajic, 1977 (Micrococcus luteus/carboxymethylcellulose), Jirku et al., 1980 (yeast cells/hydroxyalkylmethacrylate) and also by Shimizu et al., 1975 (bacterial cells/ethylene-maleic anhydride copolymer). The immobilisation of enzymes can be carried out analogously to Cannon et al., 1984 (lactate oxidase/cellulose), Clark and Bailey, 1984 (chymotrypsin/Sepharose), Ibrahim et al., 1985 (epoxy hydrolase/dextran); Beddows et al., 1981 (α-galactosidase/nylonacrylate copolymer), Raghunath et al., 1984 (urease/methacrylate-acrylate), inter alia.

In the crosslinking process, the biocatalysts are bonded to each other by bi- or poly-functional reagents, such as glutardialdehyde, diisocyanates inter alia and form characteristically insoluble, usually gelatinous aggregates of high molecular weight.

Such immobilisations of microorganisms can be carried out analogously to De Rosa et al., 1981 (bacterial cells/co-crosslinking with egg albumin by means of glutardialdehyde).

Processes for the immobilisation of enzymes that can be used within the scope of the present invention are described by Barbaric et al., 1984 (invertase/crosslinking with adipic acid dihydrazide), Talsky and Gianitsopoulos, 1984 (chymotrypsin/peptide bond between the enzyme molecules without crosslinking agent), Workman and Day, 1984 (inulinase/crosslinking of enzyme-containing cells with glutardialdehyde), Khan and Siddiqi, 1985 (pepsin/crosslinking with glutardialdehyde), Bachmann et al., 1981 (glucose isomerase/co-crosslinking with gelatine by means of glutardialdehyde), Kaul et al., 1984 (α-galactosidase/co-crosslinking with egg albumin by means of glutardialdehyde).

Matrix encapsulation comprises the inclusion of the biocatalysts in natural or synthetic polymers, which are usually of gelatinous structure. Matrix materials that are especially suitable for the inclusion of cells, organelles and spores are natural polymers such as alginate, carrageenan, pectin, agar, agarose or gelatine, since these compounds are non-toxic and protect the cells during handling.

Also suitable are synthetic polymers, such as, for example, polyacrylamides, photo-crosslinked resins inter alia. The form of the matrix encapsulation is variable within wide limits and may include, for example, spherical, cylindrical, fibrous and sheet forms.

The immobilisation of microorganisms with the aid of natural or synthetic matrix materials can be carried out as described by Mazumder et al., 1985 (bacterial cells/photo-crosslinked resins), Bettmann and Rehm, 1984 (bacterial cells/polyacrylamide hydrazide), Umemura et al., 1984 (bacterial cells/carrageenan), Karube et al., 1985 (bacterial protoplasts/agar-acetylcellulose), Cantarella et al., 1984 (yeast cells/hydroxyethylmethacrylate), Qureshi and Tamhane, 1985 (yeast cells/alginate), Deo and Gaucher, 1984 (Hyphomycetes/carrageenan), Eikmeier and Rehm, 1984 (Hyphomycetes/alginate), Bihari et al., 1984 (Hyphomycetes conidia/polyacrylamide), Vogel and Brodelius, 1984 (plant cells/alginate, agarose), Nakajima et al., 1985 (plant cells/agar, alginate, carrageenan).

The immobilisation of enzymes can be carried out analogously to Mori et al., 1972 (aminoacylase/polyacrylamide).

Membrane separation involves the creation of specific defined areas in which the reaction(s) proceed(s). The basic variants of membrane separation are differentiated as follows:

a) microencapsulation
b) liposome technique
c) the use of biocatalysts in membrane reactors.

The above-described immobilisation methods can be combined with one another, such as, for example, adsorption and crosslinking. In that case the enzymes are first of all adsorbed on a carrier and then crosslinked with one another by a bifunctional reagent.

The incubation of the biocatalysts used within the scope of the present invention with compounds of the formula III for the stereo-specific introduction of a hydroxy group into the 13$\beta$-position and/or for the 14,15-epoxidation can be carried out with the aid of processes such as those customary in applied microbiology.

In addition to the use of shake cultures there may be mentioned especially various fermenter systems that have long been established in microbiological research and industrial production.

The main task of the bioreactors is the creation of optimum hydrodynamic conditions in order to reduce the apparent Michaelis constants and to increase the reaction speed.

This is essentially achieved by maintaining an adequate relative movement between biocatalyst and surrounding medium, which increases the external mass transfer to such an extent that its hindrance in practice no longer applies.

Types of reactor that are suitable for the process concerned include, for example. stirred vessel reactors, loop-type reactors, bed reactors, fluidised bed reactors, membrane reactors and also numerous special forms of reactor, for example sieve-stirred reactors, rhomboid reactors, tube reactors inter alia (W. Hartmeier, Immobilisierte Biokatalysatoren, 1986; W. Crueger and A. Crueger, Biotechnologie-Lehrbuch der angewandten Mikrobiologie, 1984; P. Präve et al., Handbuch der Biotechnologie, 1984).

The use of stirred vessel reactors is preferred within the scope of the present invention.

Stirred vessel reactors are among the types of reactor most used in the biotechnological art of fermentation. This type of reactor ensures a rapid and thorough mixing of substrate and biocatalyst as a result of high stirring capacities and a high oxygen transfer capacity.

The advantages of stirred vessel reactors reside in their simple and thus economical construction and in their well-researched properties.

In principle, when using stirred vessel reactors two kinds of operation are possible: first of all a "batch-type" operated process, the so-called "batch" process, and, secondly, a continuous process.

In the "batch" process the biocatalysts are removed by separation or filtration once the process is complete and are either discarded (vegetative cells) or are used again in a second batch (immobilised biocatalysts).

When using the continuous process, there is a permanent continuous exchange of new substrate for the end product of the reaction. The biocatalysts must be prevented from leaving the reactor by means of suitable measures (sieve, filters, return devices).

The culturing of vegetative microorganism cells within the scope of the present invention is carried out according to known generally customary methods, liquid nutrient media preferably being used for reasons of practicability.

The composition of the nutrient media varies depending on the microorganism used. Generally, complex media with poorly defined, readily assimilable carbon(C) and nitrogen(N) sources are preferred, as customarily used, for example, also for the production of antibiotics.

In addition, vitamins and essential metal ions are necessary which, however, are as a rule contained in an adequate concentration as constituents or impurities in the complex nutrient media used.

If desired, the said constituents such as, for example, essential vitamins and also $Na^+$, $K^+$, $Ca^{2+}$, $Mg^{2+}$, $NH_4\oplus$, $PO_4^{3-}$, $SO_4^{2-}$, $Cl^-$, $CO_3^{2-}$ ions and the trace elements cobalt and manganese and zinc, inter alia, may be added in the form of their salts.

Especially suitable nitrogen sources apart from yeast extracts, yeast hydrolysates, yeast autolysates and yeast cells are especially soya meal, maize meal, oatmeal, edamine (enzymatically digested lactalbumin), peptone, casein hydrolysate, corn steep liquors and meat extracts.

The preferred concentration of the said N-sources is from 0.1 to 6 g/l.

Suitable carbon sources are, especially, glucose, lactose, sucrose, dextrose, maltose, starch, cerelose, cellulose and malt extract. The preferred concentration range is from 1.0 to 25 g/l. The use of D-glucose or soluble starch and also of cerelose as carbon source is of advantage for the hydroxylation/epoxidation process described in the following, expecially if the microorganisms used are representatives of the genus Streptomyces. Thus, for example, the following culture media are excellently suitable for representatives of the genus Streptomyces:

Medium 1

1.0 g of soluble starch
0.2 g of peptone
0.2 g of yeast extract
ad 1 l with distilled water, adjust to pH 7 with NaOH, autoclave.

Medium 2

5.0 g of D-glucose
1.0 g of peptone
0.1 g of yeast extract
ad 1 l with distilled water, adjust to pH 7 with NaOH, autoclave.

Medium 3

22.0 g of cerelose
4.0 g of Oxo Lab Lemco (Oxoid-Handbuch, 2nd edition, 1972)
5.0 g of peptone C
0.5 g of yeast extract
3.0 g of casitone (Difco Manual, 9th ed., Detroit, Difco Laboratories, 1969)
1.5 g of sodium chloride
ad 1 l with distilled water, adjust to pH 7 with NaOH, autoclave.

The above-mentioned media are also excellently suitable for culturing representatives of the genus Aspergillus and for carrying out the hydroxylation and/or epoxidation reactions.

Both the above general data about the composition of the media, and also the media listed in detail herein, serve merely to illustrate the present invention and are not of a limiting nature.

Apart from the composition of the media, the procedure used to produce the media, such as, for example, the dissolving or suspending sequence, the sterilisation of the nutrient solution as a whole or the sterilisation of the individual constituents, the prevention of contamination inter alia, also plays a significant role and should be optimised accordingly for the production process concerned.

It should also be noted that the sterilisation may cause alternations in the pH value of the nutrient medium and also precipitations.

The remaining culturing methods also correspond to the processes customarily used for culturing microorganisms.

On a small scale, the fermentations carried out within the scope of the present invention are usually in the form of shake cultures, in which case it is advantageous to use glass flasks of from 0.5 to 5 liters capacity, which contain from 0.1 to 2 liters of nutrient medium. After autoclaving and adjusting the pH to values of from pH 4 to pH 8, especially from pH 7.0 to pH 7.4, (bacteria) or to values of from pH 6 to pH 7.5 (fungi), the flasks are inoculated with the corresponding microorganism cultures under sterile conditions. The inoculation material used is generally a preculture that has been produced from preserved inoculation material in accordance with the data given below.

The cultures are advantageously grown under aerobic conditions at a temperature of from 25° to 37° C., especially 28° C., with continuous shaking at 250 rpm (revolutions per minute) on a rotatory shaking machine. After 24 hours the substrate (compounds of the formula III) is added, it being possible for the microorganisms and the substance to be hydroxylated/epoxidised to be brought into contact with one another in any manner. For practical reasons concerned with handling, it has proved advantageous to add the substrate, that is to say a compound of the formula III, to the microorganism in nutrient solution. The substance to be hydroxylated-/epoxidised can be used, for example, in powder form or in the form of a solution in a suitable solvent such as, for example, dimethylformamide, acetone or dimethyl sulphoxide or an alcoholic solvent such as, for example, methanol, ethanol or tert.-butanol (0.5 to 15% by volume, preferably 2% by volume).

The course of the reaction is continuously monitored by chromatographic methods generally used in microbiological research.

Under the above-mentioned conditions, with Streptomyces an optimum hydroxylation or epoxidation activity has generally been reached after from 2 to 6 days' culturing. It has been shown that optimum growth conditions for the microorganisms are also the optimum hydroxylation and epoxidation conditions.

The present invention also relates to the culturing of microorganisms that are capable of the stereospecific introduction of a hydroxy group into the 13β-position or of a 14,15-epoxidation of compounds of the formula III, or of both reactions, and to the incubation thereof with the said compounds in bioreactors, especially in bioreactors of the stirred vessel reactor type.

In order to ensure an optimum rate of product formation in the actual production fermenter it is recommended that the microorganisms first of all be multiplied in precultures. The number of fermenter precultures depends on the inoculation material concentration that is optimum in each particular case. Advantageously, depending on the microorganisms used, the following concentrations of inoculation material are produced for a fermenter stage: bacteria 0.1–3%, fungi 5–10%, Actinomycetales 5–10%, spore suspension $1-5 \times 10^5$ l/culture solution.

The inoculation of small fermenters (up to 20 l) is usually carried out using shaken flask precultures. In this case the total flask content is used to inoculate the fermenter.

The starting material used for the production of precultures is usually preserved inoculation material which may be, for example, in the form of lyophilisates, or of frozen or cold-stored material. The preserved inoculation material used within the scope of the present invention is preferably lyophilisate.

Multiplying the inoculation material is preferably carried out in liquid media in glass flasks on a rotatory shaking machine or, when using spores, on solid nutrient substrates. The conditions relating to nutrient substrates and culturing parameters, such as temperature, pH, introduction of oxygen inter alia, must be optimised in accordance with the microorganism or process used. The growth times for the preserved inoculation material vary from a few hours to several days depending on the starting material used.

| | |
|---|---|
| lyophilisates | 3–10 days |
| frozen preserved | 4–18 hours |
| bacteria | |
| Actinomycetales | 1–5 days |
| fungi | 1–7 days |
| cold-stored cultures | 4–24 hours |
| bacteria | |
| Actinomycetales | 1—3 days |
| fungi | 1–5 days |

If spores are used as inoculation material, the spores are first of all multiplied from preserved inoculation material on solid nutrient substrates under standardised conditions (sterile aeration, climatic chamber). If porous nutrient substrates based on peat, bran, rice or barley are used, the cultures are shaken thoroughly daily to achieve high spore densities. A further possibility lies in culturing the preserved inoculation material on nutrient media solidified by agar or other customary gelling agents, it being preferable to use nutrient media that trigger the induction of spore formation.

The sporulation time is from 7 to 30 days depending on the microorganism used and on the nutrient medium used.

To inoculate the preculture- or production-fermenters, the spores are either suspended with surface-active agents, for example a Tween 80 solution, and transferred together with their nutrient medium into the fermenter or, if solid nutrient media are used, are washed off the solid nutrient substrates also using the said surface-active agents. The spore-containing solution obtained in this manner is then used to inoculate the fermenters. Preferably, both the recovery of the spores and the inoculation of the fermenters are carried out under sterile conditions.

To produce compounds of the formulae I and II within the scope of the present invention, bioreactors of various dimensions, embracing capacities of the order of from 0.001 m$^3$ to 450 m$^3$, may be used depending on the amount of product required.

If stirred vessel bioreactors are used, then the following fermentation parameters are to be considered as critical for the course of the reaction to be optimum:

1. Temperature: The microbial hydroxylation and/or epoxidation reaction within the scope of the process according to the invention is preferably carried out in the mesophilic temperature range (temperature range of from 20° to 45° C.) The optimum temperature range for growth and product formation is from 20° to 32° C., especially from 24° to 30° C.

2. Aeration: The aeration rate is from 0.1 to 1.0 vvm (volume of air per volume of liquid per minute), preferably from 0.3 to 0.6 vvm. The aeration rate must, if necessary, be adapted to the acquired $O_2$ requirement in the course of the fermentation.

3. Pressure: Stirred vessel reactors are generally operated under slight excess pressure of from 0.2 to 0.5 bar in order to reduce the risk of contamination.

4. pH value: The pH value may vary within certain limits depending on the microorganism used. If microorganisms from the Actinomycetes group are used, the initial pH value is from pH 6 to pH 8, preferably from pH 7 to pH 7.4.

If fungi, especially fungi from the Moniliales group, are used, the initial pH of the culture solution is preferably from pH 4 to pH 8, especially from pH 6 to pH 7.5.

5. Stirring: The stirring speed depends on the type of stirrer used and the size of the fermenter. Within the scope of the present invention stirrers with impellers of the disc type are preferred which, with a stirred vessel reactor size of 0.002 m³, are operated at speeds of from 250 rpm to 450 rpm, especially from 350 rpm to 400 rpm.

Within the scope of the present invention the duration of the fermentation varies from 5 to 10 days depending on the microorganism used. The fermentation is discontinued when a majority (80-99%) of the substrate (compounds of the formula III) added at the beginning has been converted into compounds of the formula I or II or into a mixture of the two compounds.

To ascertain the optimum time for termination of the hydroxylation and/or epoxidation reaction, the course of the reaction is monitored for the whole of the fermentation by customary analysis processes, especially chromatographic processes, such as, for example, HPLC or thin layer chromatographic processes.

Processing of the fermentation broth in order to recover the hydroxylation or epoxidation products, or a mixture of the two products, can be carried out by processes customarily used in the art of fermentation (W. Crueger and A. Crueger, 1984; P. Präve, 1984).

First of all, the particulate constituents are removed from the fermentation broth using filters, centrifuges or separators.

If vegetative cells are used, the portion of the reaction products present inside the cell must be recovered. For this purpose various cell disintegration methods are available based on mechanical, thermal, chemical or enzymatic processes.

Mechanical methods suitable for use in the process according to the invention are, for example, grinding in stirred ball mills or colloid mills, the use of pressure and relaxation in a homogenizer and cell disintegration by the action of ultrasound. Non-mechanical processes include cell disintegration by drying, lysis of the cells by osmotic shock, chemical autolysis and enzymatic lysis of the cells.

Once the particulate constituents have been removed, the reaction products are concentrated by extracting the culture solution and the separated cellular constituents. For the extraction there are also numerous aids available that are customarily used in the art of fermentation, such as, for example, mixer-settlers, countercurrent columns, extraction centrifuges, among others.

It is also possible to concentrate the reaction products, for example, by membrane filtration, ultrafiltration, freeze concentration, ion exchange processes, among others.

The further processing of the crude product obtained after the extraction can be carried out by methods that are well established in microbiological and chemical research and in industrial use.

These processes include, for example, chromatographic methods, such as adsorption chromatography, ion exchange chromatography, molecular sieve chromatography, affinity chromatography, hydrophobic chromatography, partition chromatography, covalent chromatography and others, but in addition to these also various crystallisation processes. As already indicated at the beginning, the process according to the invention yields both compounds of the formula I and compounds of the formula II. Generally, mixtures of hydroxylated and epoxidised compounds are obtained, it being possible for the ratio of hydroxylated compound to epoxidised compound to be influenced by the choice of microorganism, starting material and reaction conditions (nutrient solution, organic solvent, rate of addition of the substrate, aeration). The compounds present in a mixture differ only in the region of atoms C-13, C-14 and C-15:

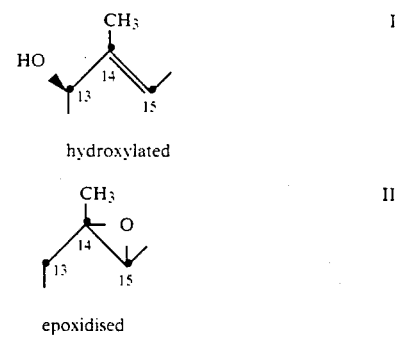

hydroxylated epoxidised and otherwise there are no differences in the molecular structure. The hydroxylated and epoxidised compounds can, as already stated, readily be isolated and separated from one another or (II) can be converted into (I).

The compounds of formulae I and II, including the novel oximes within the scope of formulae I and II, are excellently suitable for controlling pests of animals and plants, including ectoparasites of animals. These last-mentioned pests comprise those of the order Acarina, in particular pests of the families Ixodidae, Dermanyssidae, Sarcoptidae, Psoroptidae; of the orders Mallophaga, Siphonaptera, Anoplura (e.g. family of the Haematopinidae); and of the order Diptera, in particular pests of the families Muscidae, Calliphoridae, Oestridae, Tabanidae, Hippoboscidae, and Gastrophilidae.

The compounds of formulae I and II can also be used to combat hygiene pests, especially of the order Diptera (families Sarcophagidae, Anophilidae and Culicidae); of the order Orthoptera, of the order Dictyoptera (e.g.

family of the Blattidae), and of the order Hymenoptera (e.g. family of the Formicidae).

The compounds of formulae I and II also have a lasting action against mites and insects that are parasites of plants. When used to control spider mites of the order Acarina, they are effective against eggs, nymphs and adults of Tetranychidae (Tetranychus spp. and Panonychus spp.).

They also have excellent activity against sucking insects of the order Homoptera, in particular against pests of the families Aphididae, Delphacidae, Cicadellidae, Psyllidae, Coccidae, Diaspididae and Eriophydidae (e.g. the rust mite on citrus fruit); of the orders Hemiptera, Heteroptera and Thysanoptera; and against plant-feeding insects of the orders Lepidoptera, Coleoptera, Diptera and Orthoptera.

They are also suitable as soil insecticides against soil pests.

The compounds of formulae I and II are therefore effective against all developmental stages of sucking and feeding insects in crops such as cereals, cotton, rice, maize, soybeans, potatoes, vegetables, fruits, tobacco, hops, citrus fruit, avocados and others.

The compounds of formulae I and II are also effective against plant nematodes of the genera Meloidogyne, Heterodera, Pratylenchus, Ditylenchus, Radopholus, Rhizoglyphus and others.

In particular, however, the compounds act against helminths, and among these the endoparasitic nematodes can be the cause of severe diseases in mammals and fowl, for example in sheep, pigs, goats, cattle, horses, donkeys, dogs, cats, guinea pigs, cage-birds.

Typical nematodes having this indication are: Haemonchus, Trichostrongylus, Ostertagia, Nematodirus, Cooperia, Ascaris, Bunostomum, Oesophagostomum, Charbertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. The particular advantage of the compounds of formulae I and II is their activity against those parasites which are resistant to benzimidazole-based parasiticides.

Certain species of the genera Nematodirus, Cooperia and Oesophagostomum attack the intestinal tract of the host animal, whereas others of the genera Haemonchus and Ostertagia parasiticise the stomach and those of the genus Dictyocaulus the lung tissue. Parasites of the families Filariidae and Setariidae are found in internal cell tissue and organs, e.g. in the heart, blood vessels, lymph vessels and in subcutaneous tissue. In this connection, particular mention is to be made of the dog heartworm, *Dirofilaria immitis*. The compounds of formulae I and II are highly effective against these parasites.

They are also suitable for controlling pathogenic parasites in humans, among which parasites there may be mentioned as typical representatives occurring in the alimentary tract those of the genera Ancylostoma, Necator, Ascaris, Strongyloides, Trichinella, Capillaria, Trichuris and Enterobius. The compounds of this invention are also effective against parasites of the genera Wuchereria, Brugia, Onchocerca and Loa of the family of the Filariidae, which occur in the blood, in tissue and various organs, and, in addition, against Dracunculus and parasites of the genera Strongyloides and Trichinella which infest in particular the gastrointestinal tract.

The compounds of formulae I and II or mixtures of the two are used in unmodified form or, preferably, together with the adjuvants conventionally employed in the art of formulation, and are therefore formulated in known manner, for example into emulsifiable concentrates, directly sprayable or dilutable solutions, dilute emulsions, wettable powders, soluble powders, dusts, granulates, and also encapsulations in, for example, polymer substances. As with the nature of the compositions, the methods of application, such as spraying, atomising, dusting, scattering or pouring, are chosen in accordance with the intended objectives and the prevailing circumstances.

The compounds of formulae I and II are administered to warm-blooded animals at rates of application of 0.01 to 10 mg/kg of body weight, and are applied to enclosed crop areas, to pens, livestock buildings or other buildings in amounts of 10 g to 1000 g per hectare.

The formulations, i.e. the compositions, preparations or mixtures containing the active ingredient of formula I or II or containing mixtures of the two are prepared in known manner, e.g. by intimately mixing and/or grinding the active ingredients with extenders, e.g. solvents, solid carriers and, in some cases, surface-active compounds (surfactants).

Suitable solvents are: aromatic hydrocarbons, preferably fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulphoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the active ingredient to be formulated, suitable surface-active compounds are nonionic, cationic and/or anionic surfactants having good emulsifying, dispersing and wetting properties. The term "surfactants" will also be understood to include mixtures of surfactants.

Both water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g., from coconut oil or tallow oil. Further suitable surfactants are also the fatty acid methyltaurin salts.

More frequently, however, so-called synthetic surfactants are used, especially fatty sulphonates, fatty sulphates, sulphonated benzimidazole derivatives or alkylarylsulphonates.

The fatty sulphonates or sulphates are usually in the form of alkali metal salts, alkaline earth metal salts or unsubstituted or substituted ammonium salts and contain a $C_8$–$C_{22}$-alkyl radical which also includes the alkyl moiety of acyl radicals, e.g. the sodium or calcium salt of lignosulphonic acid, of dodecylsulphate, or of a mixture of fatty alcohol sulphates obtained from natural fatty acids. These compounds also comprise the salts of sulphated and sulphonated fatty alcohol/ethylene oxide adducts. The sulphonated benzimidazole derivatives preferably contain 2 sulphonic acid groups and one fatty acid radical containing 8 to 22 carbon atoms. Examples of alkylarylsulphonates are the sodium, calcium or triethanolamine salts of dodecylbenzenesulphonic acid, dibutylnaphthalenesulphonic acid, or of a condensate of naphthalenesulphonic acid and formaldehyde.

Also suitable are corresponding phosphates, e.g. salts of the phosphoric acid ester of an adduct of p-nonylphenol with 4 to 14 moles of ethylene oxide; or phospholipids.

The surfactants customarily employed in the art of formulation are described, inter alia, in the following publication: "1986 International McCutcheon's Emulsifiers and Detergents" The Manufacturing Confectioner Publishing Co., Glen Rock, N.J., U.S.A..

The pesticidal compositions usually contain 0.01 to 95%, especially 0.1 to 80%, of a compound of formula I or formula II or of a mixture of the two, 5 to 99.99% of a solid or liquid adjuvant, and 0 to 25%, especially 0.1 to 25%, of a surfactant. If a mixture of compound I and compound II is used, then the ratio of I to II is generally from 99.9:0.1 to 0.1:99.9.

Whereas commercial products are preferably formulated as concentrates, the end user will normally employ dilute formulations having an active ingredient concentration of 1–10,000 ppm.

The present invention therefore also relates to pesticidal compositions which contain as active ingredient at least one compound of formula I or of formula II, or a mixture of the two compounds, together with customary carriers and/or dispersing agents.

The compositions may also contain further ingredients such as stabilisers, antifoams, viscosity regulators, binders, tackifiers as well as fertilisers or other active ingredients for obtaining special effects.

PREPARATION EXAMPLES

H1. Preparation of a preculture of *Streptomyces violascens*

A lyophilised sample of *S. violascens* (ATCC 31560) is added to 20 ml of medium 1 in a 50 ml shaking flask, and the whole is incubated for 72 hours at 28° C. and 250 rpm. Subsequently, 2 ml of this first preculture are incubated for 48 hours in a 500 ml shaking flask with 200 ml of nutrient solution medium 1 at 28° C. and 250 rpm.

It is also possible, in a corresponding manner, to produce precultures of *S. violascens* (ATCC 31560), *S. diastatochromogenes* (ATCC 31561) and *A. niger* (ATCC 20567) using media 1, 2 and 3.

H2. Culturing conditions for the hydroxylation of milbemycin $A_4$ in a shaking flask 0.2 g of milbemycin $A_4$ is added to a 2-day-old preculture of *S. violascens* produced according to H1 in 450 ml of medium 2, and the whole is shaken at 250 rpm. at 28° C. The course of the reaction is monitored by means of HPLC (high pressure liquid chromatography) (column 25 cm/0.5 cm, eluant hexane/dimethoxyethane 3:1, 1 ml/min., UV detector 220 nm). After shaking for 4 days and a 37% conversion rate, 70% 13$\beta$-hydroxymilbemycin $A_4$ and 30% 14,15-epoxymilbemycin $A_4$ are obtained.

For working up, 200 ml of diethyl ether ($Et_2O$) are added to the reaction mixture and the whole is filtered through Hyflo Supercel ® (Super Cel; kieselguhr, purified and calcined; predominant particle size 2–25μ; Fluka Katalog No. 56678). The filter residue is carefully washed with 100 ml of $Et_2O$. The aqueous phase is extracted twice with 200 ml of $Et_2O$ each time. The combined ethereal phases are dried over $MgSO_4$ and concentrated in vacuo. The resulting crude product (0.21 g) is chromatographed on $SiO_2$ (silica gel 60, 0.040–0.063 mm) with hexane/ethyl acetate 1:1 (W. Clark-Still et al., J. Organ. Chem. 43, pp 2923, 1978) and the individual products are identified by means of 300 MHz 1H-NMR.

In a further test, with milbemycin $A_4$ and a conversion rate of 43%, this process yields a ratio of 78% 13$\beta$-hydroxymilbemycin $A_4$ to 22% 14,15-epoxymilbemycin $A_4$ (HPLC-analysis).

H3. Hydroxylation of milbemycin $A_4$ in medium 3 with 2.5% DMSO

By varying certain parameters [for example the concentration of DMSO (dimethyl sulphoxide)] it is possible to alter the balance between the reaction products (13$\beta$-hydroxy- and 14,15-epoxy-milbemycin) in favour of the hydroxy compound.

0.25 g of milbemycin $A_4$ and 5 ml of DMSO are added to a 1-day-old culture of *S. violascens* in 200 ml of medium 3 and the whole is shaken at 250 rpm. at 28° C. After 3 days, a further 50 ml of medium 3 is added. The course of the reaction is monitored by HPLC (column Kontron LiSi 60, 25 cm/0.5 cm, eluant hexane/dimethoxyethane 3:1, 1 ml/min., UV detector 220 nm). After shaking for 7 days and a 91% conversion rate, 92% 13$\beta$-hydroxymilbemycin $A_4$ and 8% 14,15-epoxymilbemycin $A_4$ are obtained.

H4. Hydroxylation of milbemycin $A_3$ and milbemycin D

If milbemycin $A_3$ or milbemycin D is reacted in an analogous manner, for example at a conversion rate of 10% a ratio of 40% 13$\beta$-hydroxymilbemycin $A_3$ and 60% 14,15-epoxymilbemycin $A_3$ is obtained or, at a conversion rate of 13%, a ratio of 29% 13$\beta$-hydroxymilbemycin D to 71% 14,15-epoxymilbemycin D is obtained (HPLC analysis).

H5. Hydroxylation of milbemycin $A_4$-5-oxime

In a manner analogous to that described above, it is also possible to convert 13-deoxy-22,23-dihydro-C-076-B1a-aglycone and compounds of the formula I in which A represents

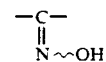

into the corresponding 13$\beta$-hydroxy compounds.

0.25 g of milbemycin $A_4$-5-oxime and 5 ml of dimethyl sulphoxide (DMSO) are added to a 1-day-old culture of *S. violascens* in 200 ml of medium 3 and the whole is shaken at 250 rpm. at 28° C. The course of the reaction is monitored by means of thin layer chromatography (precoated plates silica gel 60F Merck, eluant hexane/ethyl acetate 1:1). After shaking for 9 days no further reaction can be detected. For processing, 100 ml of dichloromethane ($CH_2Cl_2$) are added to the reaction mixture and the whole is filtered through Hyflo Supercel ®. The filter residue is washed with 50 ml of CH$_2$Cl$_2$. The aqueous phase is extracted three times with 100 ml of CH$_2$Cl$_2$ each time. The organic phases are combined, dried over MgSO$_4$ and concentrated in vacuo. The resulting crude product is chromatographed on SiO$_2$ (silica gel 60 Merck, 0.040-0.063 mm) with hexane/ethyl acetate 1:1. The 13β-hydroxymilbemycin A$_4$-5-oxime was isolated in a yield of 26%.

H6. Culturing conditions for the hydroxylation of milbemycin A$_4$ in a stirred vessel reactor To carry out the hydroxylation reaction of compounds of the formula III bioreactors of the stirred vessel reactor type marketed by MBR (Switzerland), Modell Mini, are used. These reactors have a capacity of 2 litres and are fitted with stirrers of the disk type. Aeration is effected by means of sterile-filtered compressed air.

Before fermentation commences, the reactor and the culture medium (medium 3) are autoclaved separately. The pH value is then adjusted to pH 7.0 to 7.4 by the addition of a sterile 2N NaOH solution under sterile conditions. After the fermentation medium has cooled, the fermentation is initiated by the addition of 200 ml of a 3-day-old preculture of *S. violascens* in medium 3 and by the addition of 1.5 g of milbemycin A$_4$, dissolved in 10 ml of DMSO. The inoculation of the production fermenter is also carried out under sterile conditions.

The fermentation is carried out at a temperature of 28° C. and an aeration rate of 0.44 vvm. The stirring speed is 400 rpm. For the whole of the incubation period, 100 ml of fresh culture medium 3 are introduced into the fermentation medium daily under sterile conditions.

The course of the reaction is followed for the entire fermentation with the aid of chromatographic analyses (HPLC). After a total incubation time of 9 days, 86% of the milbemycin A$_4$ added at the beginning of fermentation has reacted. 61% of the reacted milbemycin A$_4$ could be identified by means of HPLC as 13β-hydroxymilbemycin A$_4$, and 8% as 14,15-epoxymilbemycin A$_4$.

When the fermentation is complete, 400 ml of methylene chloride (CH$_2$Cl$_2$) are added to the reaction mixture and the whole is filtered through Hyflo Supercel ®. The filtrate obtained in this manner is then continuously extracted with methylene chloride. After 48 hours the organic phase is separated off, dried over MgSO$_4$ and concentrated in vacuo.

The resulting crude product is then purified in accordance with the process described in Example H2, with the aid of chromatographic methods.

TABLE 1

Typical representatives of compounds of formula I

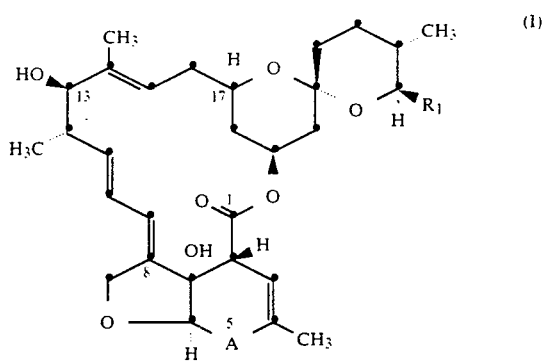

| Comp. No. | R$_1$ | A |
|---|---|---|
| 1.1 | C$_2$H$_5$ | —CH—<br>\|<br>OH |
| 1.2 | CH$_3$ | —CH—<br>\|<br>OH |
| 1.3 | isoC$_3$H$_7$- | —CH—<br>\|<br>OH |
| 1.4 | sec.C$_4$H$_9$ | —CH—<br>\|<br>OH |
| 1.5 | CH$_3$ | —C—<br>\|\|<br>N—OH |
| 1.6 | isoC$_3$H$_7$ | —C—<br>\|\|<br>N—OH |
| 1.7 | C$_2$H$_5$ | —C—<br>\|\|<br>N—OH |
| 1.8 | sek.C$_4$H$_9$ | —C—<br>\|\|<br>N—OH |

TABLE 2

Typical representatives of compounds of formula II

| Comp. No. | R₁' | A' |
|---|---|---|
| 2.1 | C₂H₅ | —CH(OH)— |
| 2.2 | CH₃ | —CH(OH)— |
| 2.3 | isoC₃H- | —CH(OH)— |
| 2.4 | sec.C₄H₉ | —CH(OH)— |
| 2.5 | CH₃ | —C(=N—OH)— |
| 2.6 | isoC₃H- | —C(=N—OH)— |
| 2.7 | C₂H₅ | —C(=N—OH)— |
| 2.8 | sek.C₄H₉ | —C(=N—OH)— |

FORMULATION EXAMPLES (throughout percentages are by weight)

| F1. Wettable powders | a) | b) | c) |
|---|---|---|---|
| an active compound from Tables 1 and 2 | 25% | 50% | 75% |
| sodium lignosulphonate | 5% | 5% | — |
| sodium laurylsulphate | 3% | — | 5% |
| sodium diisobutylnaphthalenesulphonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active compound is thoroughly mixed with the adjuvants and the mixture is thoroughly ground in a suitable mill, affording wettable powders which can be diluted with water to give suspensions of the desired concentration.

| F2. Emulsifiable concentrate | |
|---|---|
| an active compound from Tables 1 and 2 | 10% |
| octylphenol polyethylene glycol ether (4-5 moles of ethylene oxide) | 3% |
| calcium dodecylbenzenesulphonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| F3. Dusts | a) | b) |
|---|---|---|
| an active compound from Tables 1 and 2 | 5% | 8% |
| talcum | 95% | — |
| kaolin | — | 92% |

Ready for use dusts are obtained by mixing the active compound with the carrier and grinding the mixture in a suitable mill.

| F4. Extruder granulate | |
|---|---|
| an active compound from Tables 1 and 2 | 10% |
| sodium lignosulphonate | 2% |
| carboxymethylcellulose | 1% |
| kaolin | 87% |

The active compound is mixed and ground with the adjuvants, and the mixture is subsequently moistened with water. The mixture is extruded and then dried in a stream of air.

| F5. Tablets or boli | | |
|---|---|---|
| I | an active compound from Tables 1 and 2 | 33.00% |
| | methylcellulose | 0.80% |
| | highly dispersed silicic acid | 0.80% |
| | maize starch | 8.40% |

The methylcellulose is stirred in water and allowed to swell. Then the silicic acid is stirred in to give a homogeneous suspension. The active compound and the maize starch are mixed and the aqueous suspension is added to the mix, which is kneaded to a paste. This paste is granulated through a 12M sieve and the granulate is then dried.

| II | crystalline lactose | 22.50% |
|---|---|---|
| | maize starch | 17.00% |
| | microcrystalline cellulose | 16.50% |
| | magnesium stearate | 1.00% |

All 4 adjuvants are thoroughly mixed.
Phases I and II are mixed and compressed to tablets or boli.

If the active compounds or compositions containing them are used for controlling endoparasitic nematodes, cestodes and trematodes in domestic animals and productive livestock, for example cattle, sheep, goats, cats and dogs, they can be administered to the animals in both single and repeated doses. Depending on the species of animal, the individual does are preferably administered in amounts ranging from 0.1 to 10 mg/kg of body weight. A better action is often achieved by protracted administration, or lower total doses may also suffice. The active compounds, or compositions containing them, can also be added to feeds and drinks. The ready-prepared feeds contain the active compound combinations preferably in a concentration of 0.005 to 0.1 percent by weight. The compositions can be administered to the animals perorally in the form of solutions, emulsions, suspensions, powders, tablets, boli or capsules. If the physical and toxicological properties of solutions or emulsions permit it, the active compounds, or compositions containing them, can also be administered to animals for example intraruminally or by subcutaneous injection, or can be applied to the bodies of the animals by the pour-on method. Administration of the active compound to animals by means of salt licks or molasses blocks is also possible.

BIOLOGICAL EXAMPLES

B-1. Insecticidal stomach poison action against *Spodoptera littoralis*

Potted cotton plants at the 5-leaf stage are sprayed with a solution containing 3, 12.5 or 50 ppm of the test compound in acetone/water.

After the coating has dried, the plants are populated with about 30 larvae ($L_1$ stage) of *Spodoptera littoralis*. Two plants are used for each test compound and test species. The test is carried out at about 24° C. and 60% relative humidity. Evaluations and intermediate evaluations of moribund insects, larval growth and feeding damage are made after 24, 48 and 72 hours.

Compounds within the scope of formulae I and II (Tables 1 and 2), especially the novel oximes according to the invention, were 100% effective at a rate of application of 12.5 ppm.

B-2. Action against plant-destructive acarids: OP-sensitive *Tetranychus urticae*

16 hours before the start of the test, the primary leaves of bean plants (*Phaseolus vulgaris*) are infected with an infested piece of leaf from a mass culture of *Tetranychus urticae*. Upon removal of the piece of leaf, the plants infested with all stages of the mites are sprayed to drip point with a solution containing 0.8 ppm of the test compound. The temperature in the greenhouse compartment is about 25° C.

The percentage of mobile stages (adults and nymphs) and of eggs is evaluated under a stereoscopic microscope after 7 days.

Compounds within the scope of formulae I and II (Tables 1 and 2) especially the novel oximes of the invention, achieve a 60% to 100% kill at the active ingredient concentration used.

B-3. Action against $L_1$ larvae of *Lucilia sericata*

1 ml of an aqueous suspension of test compound is mixed with 3 ml of a special larval culture medium at about 50° C. such that a homogeneous composition is obtained. About 30 Lucilia larvae ($L_1$) are put into each test tube containing active ingredient. A mortality count is made after 4 days. The compounds of formulae I and II achieve a good action against $L_1$ larvae of *Lucilia sericata*. The novel oxime compounds of the invention exhibit 100% effectiveness at application rates of only 250 ppm.

B-4. Acaricidal action against *Boophilus microplus* (Biarra strain)

Adhesive tape is so applied horizontally across a PVC plate that 10 fully replete female *Boophilus microplus* ticks (Biarra strain) can be affixed thereto on their backs, side by side, in a row. Each tick is injected from an injection needle with 1 $\mu$l of a liquid which represents a 1:1 mixture of polyethylene glycol and acetone, in which mixture a specific amount of active compound of 1, 0.5 or 0.1 $\mu$g per tick is dissolved. Control ticks are injected with liquid that does not contain the active ingredient. After this treatment, the ticks are kept in an insectarium under normal conditions at about 28° C. and 80% relative humidity until oviposition has taken place and the larvae have hatched from the eggs of the control ticks.

The activity of the test compound is determined with the $IR_{90}$, i.e. the effective dose is determined at which 9 out of 10 female ticks (90%) even after 30 days lay eggs from which larvae are unable to hatch.

Compounds of formulae I and II (Tables 1 and 2) exhibit a good activity against *Boophilus microplus* with an $IR_{90}$ of 1 $\mu$g. The novel oxime compounds of the invention reach their $IR_{90}$ value at very low rates of application (0.5 $\mu$g).

B-5. Trial with sheep infected with nematodes (*Haemonchus concortus* and *Trichostrongylus colubriformis*)

The test compound is administered in the form of a suspension with a stomach probe or by intraruminal injection to sheep which have been artificially infected with *Haemonchus concortus* and *Trichostrongylus colubriformis*. 1 to 3 animals are used for each dose. Each sheep is treated only once with a single dose of 1 mg or 0.5 mg/kg of body weight as desired. Evaluation is made by comparing the number of worm eggs excreted in the faeces of the sheep before and after treatment.

Sheep infected simultaneously and in the same manner but untreated are used as controls. In comparison with untreated and infected control groups, there is a reduction in nematode infestation in the range of from 60 to 100% (100% =complete reduction of the number of worm eggs in the faeces) in sheep which have been treated with one of the compounds according to Tables 1 and 2 at a rate of application of 1 mg/kg.

B-6. Contact action against *Aphis craccivora*

Pea plantlets which have been infested with all development stages of the aphids are sprayed with a solution prepared from an emulsifiable concentrate of the test compound and containing 50 ppm, 25 ppm or 12.5 ppm of active ingredient. After 3 days evaluation is made to establish whether more than 80% of the aphids are dead or have dropped from the plants. A composition is rated as effective at that level of activity only.

Compounds of formulae I and II of the Tables, especially also the novel oxime compounds of the invention, achieve complete kill (=100%) even at low concentrations of from 12.5 ppm to 25 ppm.

B-7. Larvicidal action against *Aedes aegypti*

A 0.1% solution of the test compound in acetone is pipetted onto the surface of 150 ml of water in beakers in amounts sufficient to give concentrations of 10 ppm, 3.3 ppm and 1.6 ppm. After the acetone has evaporated, about 30 to 40 three-day-old Aedes larvae are put into each beaker. Mortality counts are made after 1, 2 and 5 days.

In this test, compounds of formulae I and II of the Tables achieved complete kill of all larvae after 1 day even at low concentrations of from 3.3 to 10 ppm.

B-8. Milbicidal action against *Dermanyssus gallinae*

2 to 3 ml of a test solution (100, 10, 1 and 0.1 ppm of test compound) are put into a glass container which is open at the top and about 200 mites in different stages of development are put into this container. The container is then sealed with cotton wool and shaken uniformly for 10 minutes until the mites are completely wetted. The container is then inverted until excess test solution has been absorbed by the cotton wool. The container is again inverted and the treated mites are kept under observation for 3 days under laboratory conditions to evaluate the effectiveness of the test compounds. Mortality is the criterion for effectiveness.

Compounds within the scope of formulae I and II effect 100% kill at a concentration of 100 ppm.

LITERATURE

Angelino S. A. G. F., Müller F., Plas H. C. van der (1985) Purification and immobilization of rabbit liver aldehyde oxidase. Biotechnol. Bioeng 27: 447–455.

Bachmann S., Gebicka L., Gasyna Z., (1981) Immobilization of glucose isomerase on radiation-modified gelatine gel. Starch/Stärke 33: 63–66.

Barbaric S., Kozulic B., Leustek I., Pavlovic B., Cesi V., Mildner P. (1984) Crosslinking of glycoenzymes via their carbohydrate chains. In: 3rd Eur. Congr. Biotechnol., Vol. 1. Verlag Chemie, Weinheim, p. 307–312.

Beddows C. G., Guthrie J. T., Abdel-Hay F. I. (1981) The use of graft copolymers as enzyme supports immobilization of proteins and enzymes on a hydrolyzed nylon-coacrylonitrile system. Biotechnol. Bioeng 23: 2885–2889.

Bettmann H., Rehm H. J. (1984) Degradation of phenol by polymer entrapped microorganisms. Appl. Microbiol. Biotechnol. 20: 285–290.

Bihari V., Goswami P. P., Rizvi S. H. M., Kahn A. W., Basu S. K., Vora V. C. (1984) Studies on immobilized fungal spores of microbial transformation of steroids: 11a-hydroxylation of progesterone with immobilized spores of Aspergillus ochraceus G8 on polyacrylamide gel and other matrices. Biotechnol. Bioeng 26: 1403–1408.

Black G. M., Webb C., Matthews T. M., Atkinson B. (1984) Practical reactor systems for yeast cell immobilization using biomass support particles. Biotechnol. Bioeng 26: 134–141.

Cabral J. M. S., Novais J. M., Cardoso J. P. (1984) Coupling of glucoamylase on alkylamine derivative of titanium(IV) activated controlled pore glass with tannic acid. Biotechnol. Bioeng 26: 386–388.

Cannon J. J., Chen L-F, Flickinger M. C., Tsao G. T. (1984) The development of an immobilized lactate oxidase system for lactic acid analysis. Biotechnol. Bioeng 26: 167–173.

Cantarella M., Migliaresi C., Tafuri M. G., Afani F. (1984) Immobilization of yeast cells in hydroxymethacrylate gels. Appl. Microbiol. Biotechnol. 20: 233–237.

Chipley J. R. (1974) Effects of 2,4-dinitrophenol and N,N'-dicyclohexylcarbodiimide on cell envelope-associated enzymes of *Escherichia coli* and *Salmonella enteritidis*. Microbios. 10: 115–120.

Clark-Still W., Kahn M., Mitra A. (1978) J. Org. Chem. 43: 2923

Crueger W., Crueger A. (1984) Biotechnologie-Lehrbuch der angewandten Mikrobiologie, 2nd edition, R. Oldenbourg Verlag Munich, Vienna, 1984.

Deo Y. M., Gaucher G. M. (1984) Semicontinuous and continuous production of penicillin-G by Penicillium chrysogenum cells immobilized in k-carrageenin beads. Biotechnol. Bioeng 26: 285–295.

De Rosa M., Gambacorta A., Lama L., Nicolaus B. (1981) Immobilization of thermophilic microbial cells in crude egg white. Biotechnol. Lett 3: 183–188.

DiLuccio R. C., Kirwan D. J. (1984) Effect of dissolved oxygen on nitrogen fixation by A. Vinelandii. II. Ionically adsorbed cells. Biotechnol. Bioeng 26: 87–91.

Erhardt H. M., Rehm H. J. (1985) Phenol degradation by microorganisms adsorbed on activated carbon. Appl. Microbiol. Biotechnol. 21: 32–36.

Eikmeier H., Rehm H. J. (1984) Production of citric acid with immobilized Aspergillus niger. Appl. Microbiol. Biotechnol. 20: 365–370.

Förberg C., Häggström L. (1984) Adsorbed cell systems controlled by the nutrient dosing technique. In: 3rd Eur. Congr. Biotechnol. Vol. 2. Verlag Chemie, Weinheim, p. 115–120.

Gainer J. L., Kirwan D. J., Foster J. A., Seylan E. (1980) Use of adsorbed and covalently bound microbes in reactors. Biotechnol. Bioeng Symp 10: 35–42.

Giard D. J., Loeb D. H., Thilly W. G., Wang D. I. C., Levine D. W. (1979) Human interferon production with diploid fibroblast cells grown on microcarriers. Biotechnol. Bioeng 21: 433–442.

Hartmeier W. (1986), Immobilisierte Biokatalysatoren. Springer Verlag, Berlin, Heidelberg, New York, Tokyo, 1986.

Hofstee B. H. J. (1973) Immobilization of enzymes through non-covalent binding to substituted agaroses. Biochem. Biophys. Res. Commun. 53: 1137–1144.

Ibrahim M., Hubert P., Dellacherie E., Magadalou J., Muller J., Siest G. (1985) Covalent attachment of epoxide hydrolase to dextran. Enz. Microbiol. Technol. 7: 66–72.

Jack T. R., Zajic J. E. (1977) The enzymatic conversion of L-histidine to urocanic acid by whole cells of Micrococcus luteus immobilized on carbodiimide activated carboxymethylcellulose. Biotechnol. Bioeng 19: 631.

Jirku V., Turkova J., Krumphanzl V. (1980) Immobilization of yeast with retention of cell division and extracellular production of macromolecules. Biotechnol. Lett. 2: 509–513.

Karube I., Aizawa K., Ikeda S., Suzuki S (1979) Carbon dioxide fixation by immobilized chloroplasts. Biotechnol. Bioeng 21: 253–260.

Kato T., Horikoshi K. (1984) Immobilized cyclomaltodextrin glucanotransferase of an alkalophilic Bacillus sp no 38-2. Biotechnol. Bioeng 26: 595–598.

Kaul R., D'Souza S. F., Nadkarni G. B. (1984) Hydrolysis of milk lactose by immobilized ?-galactosidase-hen egg white powder. Biotechnol. Bioeng 26: 901–904.

Khan S. S., Siddiqi A. M. (1985) Studies on chemically aggregated pepsin using glutaraldehyde. Biotechnol. Bioeng 27: 415–419.

Krakowiak W., Jach M., Korona J., Sugier H. (1984) Immobilization of glucoamylase on activated aluminium oxide. Starch/Stärke 36: 396–398.

Kühn W., Kirstein D., Mohr P. (1980) Darstellung und Eigenschaften trägerfixierter Glukoseoxydase. Acta Biol. med. Germ. 39: 1121–1128.

Mazumder T. K., Sonomoto K., Tanaka A., Fukui S. (1985) Sequential conversion of cortexolone to prednisolone by immobilized mycelia of Curvularia lunata and immobilized cells of Arthrobacter simplex. App. Microbiol. Biotechnol. 21: 154–161.

Messing R. A., Oppermann R. A. (1979) Pore dimensions for accumulating biomass. I. Microbes that reproduce by fission or budding. Biotechnol. Bioeng 21: 49–58.

Miyawaki O., Wingard jr L. B. (1984) Electrochemical and enzymatic activity of flavin dinucleotide and glucose oxidase immobilized by adsorption on carbon. Biotechnol. Bioeng 26: 1364–1371.

Monsan P., Combes D., Alemzadeh I. (1984) Invertase covalent grafting onto corn stover. Biotechnol. Bioeng 26: 658–664.

Mori T., Sato T., Tosa T., Chibata I. (1972) Studies on immobilised enzymes. X. Preparation and properties of aminoacylase entrapped into acrylamide gel-lattice. Ezymologia 43: 213–226.

Nakajima H., Sonomoto K., Usui N., Sato F., Yamada Y., Tanaka A., Fukui S., (1985) Entrapment of Lavendula vera and production of pigments by entrapped cells. J. Biotechnol. 2: 107–117.

Navarro J. M., Durand G. (1977) Modification of yeast metabolism by immobilization onto porous galss. Eur. J. Appl. Microbiol. Biotechnol. 4: 243–254.

Präve P., Faust U., Sittig W., Sukatsch. D. A. (1984) Handbuch Biotechnologie. 2nd edition, R. Oldenbourg Verlag Munich, Vienna, 1984.

Qureshi N., Tamhane D. V. (1985) Production of mead by immobilized whole cells of *Saccharomyces cerevisiae*. Appl. Microbiol. Biotechnol 21: 280–281.

Raghunath K., Rao K. P., Joseph U. T. (1984) Preparation and characterization of urease immobilized onto collagen-poly(glycidyl methacrylate) graft copolymer. Biotechnol. Bioeng 26: 104–109.

Romanovskaya V. A., Karpenko V. I., Pantskhava E. S., Greenberg T. A., Malashenko Y. R. (1981) Catalytic properties of immobilized cells of methane-oxidizing and methanogenic bacteria. In: Moo-Young M. (Hrsg) Advances in Biotechnology. Vol. 3 Pergamon. Toronto, p. 367–372.

Shimizu S., Morioka H., Tani Y., Ogata K. (1975) Synthesis of coenzyme A by immobilized microbial cells. J. Ferm. Technol. 53: 77–83.

Talsky G., Gianitsopoulos G. (1984) Intermolecular crosslinking of enzymes. In: 3rd Eur. Congr. Biotechnol., Vol. 1, Verlag Chemie, Weinheim, p. 299–305.

Umemura I., Takamatsu S., Sato T., Tosa T., Chibata I. (1984) Improvement of production of L-aspartic acid using immobilized microbial cells. Appl. Microbiol. Biotechnol. 20: 291–295.

Van Haecht J. L., Bolipombo M., Rouxhet P. G. (1985) Immobilization of Saccaromyces cerevisiae by adhesion: treatment of the cells by AI ions. Biotechnol. Bioeng. 27: 217–224.

Vogel H. J., Brodelius P. (1984) an in vivo 31P NMR comparison of freely suspended and immobilized Catharanthus roseus plant cells. J. Biotechnol. 1: 159–170.

Weetall H. H., Mason R. D. (1973) Studies on immobilized papain. Biotechnol. Bioeng. 15: 455–466.

Wiegel J., Dykstra M. (1984) Clostridium thermocellum: adhesion and sporulation while adhered to cellulose and hemicellulose. Appl. Microbiol. Biotechnol. 20: 59–65.

Workman W. E., Day D. F. (1984) Enzymatic hydrolysis of inulin to fructose by glutaraldehyde fixed yeast cells. Biotechnol. Bioeng. 26: 905–910.

CITED PATENT LITERATURE

U.S. Pat. No. 4,226,941

EP 0,147,852

EP 0,180,539

EP 0,184,989

EP 0,184,173

U.S. Pat. No. 3,950,360

U.S. Pat. No. 4,346,171

U.S. Pat. No. 4,547,520

U.S. Pat. No. 4,173,571

DE-S 35 32 794

U.S. Pat. No. 4,328,335.

We claim:

1. A one-step microbial process for the preparation of 13β-hydroxy-milbemycins or 14,15-epoxy-milbemycins of formulas I or II:

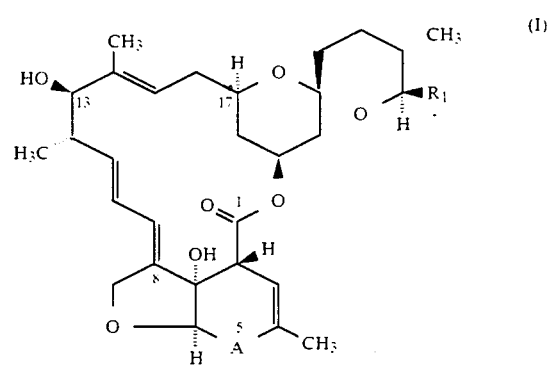

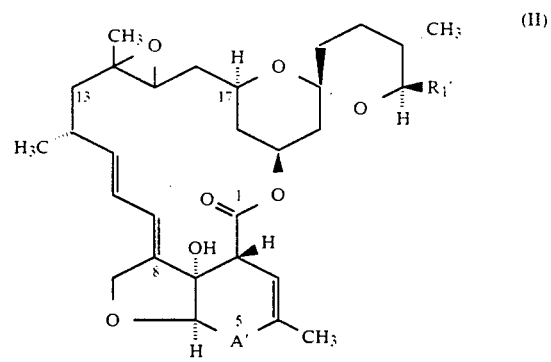

in which $R_1$ and $R_1'$ are methyl or isopropyl and A and A' are —CH(OH)—, or $R_1$ and $R_1'$ are ethyl and A and A' are —CH(OH)— or —C(=N–OH)—, or a mixture of compounds of formulas I and II, which process comprises bringing a milbemycin of formula III

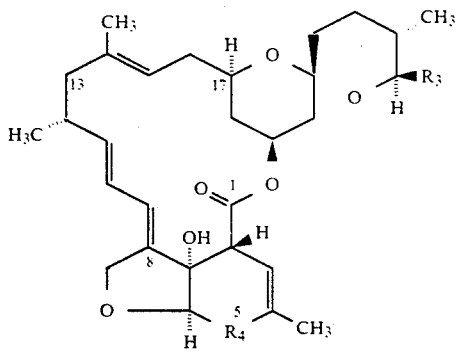

(III)

dissolved in a liquid phase, in which $R_3$ is $R_1$ or $R_1'$ and $R_4$ is A or A', and $R_1$, $R_1'$, A and A' have the meanings given for formulas I and II, into contact with a microorganism selected from the group consisting of *Streptomyces diastatochromogenes* ATCC 31561, *Streptomyces violascens* ATCC 31560 and *Aspergillus niger* ATCC 20567 that is capable of 13β-hydroxylation or 14,15-epoxidation, or of both reactions, for a period of time that is sufficient for carrying out the 13β-hydroxylation or 14,15-epoxidation reaction or both reactions, and isolating the reaction product.

2. A process of claim 1, wherein the microorganism is *Streptomyces violascens* ATCC 31560.

3. A process of claim 1, wherein the microorganism is *Streptomyces diastatochromogenes* ATCC 31561.

4. A process of claim 1, wherein the microorganism is *Aspergillus niger* ATCC 20567.

5. A process of claim 1, wherein the microorganism is in immobilized form.

6. A process of claim 1, wherein the hydroxylation or epoxidation reaction or both reactions are carried out in a bioreactor.

7. A process of claim 6, wherein the bioreactor is a stirred vessel reactor.

8. A process of claim 1, wherein the process temperature is in the range of 20° C. to 32° C.

9. A process of claim 1, wherein the milbemycin of formula III is brought into contact with the microorganism in a culture medium at a pH in the range of 4 to 8.

10. A process of claim 1, wherein the milbemycin of formula III is brought into contact with the microorganism in a culture medium having a nitrogen source at a concentration in the range of 0.1 g/l to 6 g/l.

11. A process of claim 1, wherein the milbemycin of formula III is brought into contact with the microorganism in a culture medium having a carbon source at a concentration in the range of 1.0 g/l to 25 g/l.

* * * * *